United States Patent
Park et al.

(10) Patent No.: US 10,911,393 B2
(45) Date of Patent: Feb. 2, 2021

(54) METHOD AND SYSTEM FOR BUILDING USER CONFIDENCE

(71) Applicant: LINE Plus Corporation, Seongnam-si (KR)

(72) Inventors: Youngsub Park, Seongnam-si (KR); Su Ahn Lee, Seongnam-si (KR); JaeYun Jung, Seongnam-si (KR); Seung Wook Han, Seongnam-si (KR); Hee Jong Lee, Seongnam-si (KR)

(73) Assignee: LINE PLUS CORPORATION, Seongnam-si (KR)

( * ) Notice: Subject to any disclaimer, the term of this patent is extended or adjusted under 35 U.S.C. 154(b) by 0 days.

(21) Appl. No.: 16/706,262

(22) Filed: Dec. 6, 2019

(65) Prior Publication Data

US 2020/0204516 A1 Jun. 25, 2020

(30) Foreign Application Priority Data

Dec. 24, 2018 (KR) .................. 10-2018-0168412

(51) Int. Cl.
| | |
|---|---|
| *H04L 12/58* | (2006.01) |
| *G16H 20/70* | (2018.01) |
| *H04L 29/08* | (2006.01) |
| *A61B 5/16* | (2006.01) |
| *G16H 40/67* | (2018.01) |

(52) U.S. Cl.
CPC .............. *H04L 51/32* (2013.01); *A61B 5/165* (2013.01); *G16H 20/70* (2018.01); *G16H 40/67* (2018.01); *H04L 67/22* (2013.01)

(58) Field of Classification Search
None
See application file for complete search history.

(56) References Cited

U.S. PATENT DOCUMENTS

| | | | |
|---|---|---|---|
| 9,367,878 B2* | 6/2016 | Rao | G06Q 50/01 |
| 9,684,775 B2* | 6/2017 | Gupta | H04W 12/08 |
| 10,321,283 B2* | 6/2019 | Johnson | H04W 4/029 |
| 10,764,340 B2* | 9/2020 | Ritchie | G06F 16/9535 |
| 2013/0325745 A1* | 12/2013 | Kelly | G06Q 50/01 705/347 |
| 2015/0302103 A1* | 10/2015 | Jeremias | G06F 3/04842 715/758 |
| 2015/0319203 A1* | 11/2015 | Jeremias | G06Q 30/0641 715/753 |
| 2020/0195694 A1* | 6/2020 | Kalinin | H04L 63/1416 |

FOREIGN PATENT DOCUMENTS

KR 10-2010-0109847 10/2010

* cited by examiner

*Primary Examiner* — Sargon N Nano
(74) *Attorney, Agent, or Firm* — Staas & Halsey LLP

(57) ABSTRACT

Provided is a method and system for building a user confidence. A user confidence building method of a computer apparatus including at least one processor may include storing a confidence assigned to each of users; monitoring an activity of each of the users in a service; adjusting a confidence of a first user based on an incoming edge of the first user that is formed by an activity of a second user for the first user; and propagating the adjusted confidence of the first user based on an outgoing edge of the first user in response to adjusting the confidence of the first user.

18 Claims, 5 Drawing Sheets

METHOD AND SYSTEM FOR BUILDING USER CONFIDENCE

CROSS-REFERENCE TO RELATED APPLICATION(S)

This U.S. non-provisional application claims the benefit of priority under 35 U.S.C. § 119 to Korean Patent Application No. 10-2018-0168412 filed on 2018 Dec. 24, in the Korean Intellectual Property Office (KIPO), the entire contents of which are incorporated herein by reference.

BACKGROUND

Field

One or more example embodiments relate to technology for building a user confidence, and more particularly, to a user confidence building method that may adjust a confidence of a user based on an incoming edge of the user formed by an activity of another user for the user, a computer apparatus for performing the method, and a non-transitory computer-readable storage medium including computer instructions to perform the user confidence building method.

Description of Related Art

There are techniques for determining a user based on data about aggressive actions (e.g., activities such as posting content and participating) of a user at a service. For example, a method of evaluating a user reputation through a social network and a system and method for evaluating a content reputation using the same are disclosed in Korean Patent Laid-Open Publication No. 10-2010-0109847.

However, in the related art, data about actions of a user is adjustable according to the intent of the user and thus, an abusing probability is relatively high. For example, if a confidence of the user is determined based on an activity that the user regards content of another user or registers another user as a friend or a neighbor, an abusing that the user performs such activities to increase the confidence of the user not for purposes of a service may occur, which may lead to degrading the objectivity about the user confidence.

SUMMARY

One or more example embodiments provide a user confidence building method that may adjust a confidence of a user based on an incoming edge of the user formed by an activity of another user for the user, a computer apparatus for performing the method, and a non-transitory computer-readable storage medium including computer instructions to perform the user confidence building method.

According to an aspect of at least one example embodiment, there is provided a user confidence building method of a computer apparatus including at least one processor, the method including: storing, by the at least one processor, a confidence assigned to each of users; monitoring, by the at least one processor, an activity of each of the users in a service; adjusting, by the at least one processor, a confidence of a first user based on an incoming edge of the first user that is formed by an activity of a second user for the first user; and propagating, by the at least one processor, the adjusted confidence of the first user based on an outgoing edge of the first user in response to adjusting the confidence of the first user. According to an aspect of at least one example embodiment, there is provided method by a computer apparatus comprising at least one processor, the method, by the at least one processor, including storing, for each user of a plurality of users of a service provided through electronic devices, information indicating a confidence assigned to the user that represents an evaluation of the user based on monitored activities of the user in the service; forming an incoming edge for a first user, among the plurality of users, based on monitoring an activity of a second user, among the plurality of users, that represents a directed activity in the service of the second user towards the first user; adjusting the confidence of the first user indicated by the stored information based on the formed incoming edge; based on the adjusted confidence of the first user, forming an outgoing edge for the first user that represents a directed activity in the service towards another user, among the plurality of users; and propagating the adjusted confidence of the first user in the stored information based on the formed outgoing edge for the first user.

The adjusting of the confidence of the first user may include determining an adjustment level of the confidence of the first user based on at least one of an attribute of the activity of the second user that forms the incoming edge and a confidence of the second user.

The adjusting of the confidence of the first user may include increasing the confidence of the first user based on a positive activity of the second user for the first user and decreasing the confidence of the first user based on a negative activity of the second user for the first user.

The positive activity may include at least one activity among a (1-1)-th activity that the second user initially sends a message to the first user, a (1-2)-th activity that the second user adds the first user as a personal relationship of the service, a (1-3)-th activity that the second user invites the first user to a chatroom or a community in which the second user participates, a (1-4)-th activity that the second user adds the first user to favorite, and a (1-5)-th activity that the second user creates a comment on a posting of the first user. The negative activity may include at least one activity among a (2-1)-th activity that a frequency at which the second user sends a message to the first user decreases, a (2-2)-th activity that the second user excludes the first user from the personal relationship of the service, a (2-3)-th activity that the second user excludes the first user from the chatroom or the community in which the second user participates, a (2-4)-th activity that the second user excludes the first user from the favorite, and a (2-5)-th activity that the second user deletes the comments created by the second user on the posting of the first user.

The propagating of the adjusted confidence of the first user may include readjusting a confidence of a third user that is adjusted based on the outgoing edge of the first user that is formed by an activity of the first user for the third user.

The user confidence building method may further include readjusting the confidence of the first user based on an adjusted confidence of the second user that is propagated through the incoming edge of the first user in response to adjusting the confidence of the second user.

The adjusting of the adjusted confidence of the first user may include readjusting the confidence of the first user in response to imposing a penalty to the first user at the service or readjusting the confidence of the first user based on an adjusted confidence of the second user that is propagated through the incoming edge of the first user as the confidence of the second user is readjusted in response to imposing a penalty to the second user at the service.

The propagating of the adjusted confidence of the first user may include adjusting a rate at which the adjusted confidence of the first user is propagated based on an attribute of the activity of the second user for the first user.

The user confidence building method may further include determining whether the first user is an abuser based on the adjusted confidence of the first user.

The user confidence building method may further include determining a new service to be provided to the first user based on the adjusted confidence of the first user.

According to an aspect of at least one example embodiment, there is provided a non-transitory computer-readable storage medium storing computer instructions that, when executed by a processor, cause the processor to perform the user confidence building method.

According to an aspect of at least one example embodiment, there is provided a computer apparatus including at least one processor configured to execute a computer-readable instruction on the computer apparatus. The at least one computer processor is configured to store a confidence assigned to each of users, monitor an activity of each of the users in a service, adjust a confidence of a first user based on an incoming edge of the first user that is formed by an activity of the second user for the first user, and propagate the adjusted confidence of the first user based on an outgoing edge of the first user in response to adjusting the confidence of the first user.

According to some example embodiments, the objectivity about a confidence may be secured by adjusting a confidence of a user based on an incoming edge of the user that is formed by an activity of another user for the user and by evaluating the user based on actions in terms of passiveness of the user, which are activities of other users for the user.

Further areas of applicability will become apparent from the description provided herein. The description and specific examples in this summary are intended for purposes of illustration only and are not intended to limit the scope of the present disclosure.

BRIEF DESCRIPTION OF THE FIGURES

Example embodiments will be described in more detail with regard to the figures, wherein like reference numerals refer to like parts throughout the various figures unless otherwise specified, and wherein.

Figure 1:
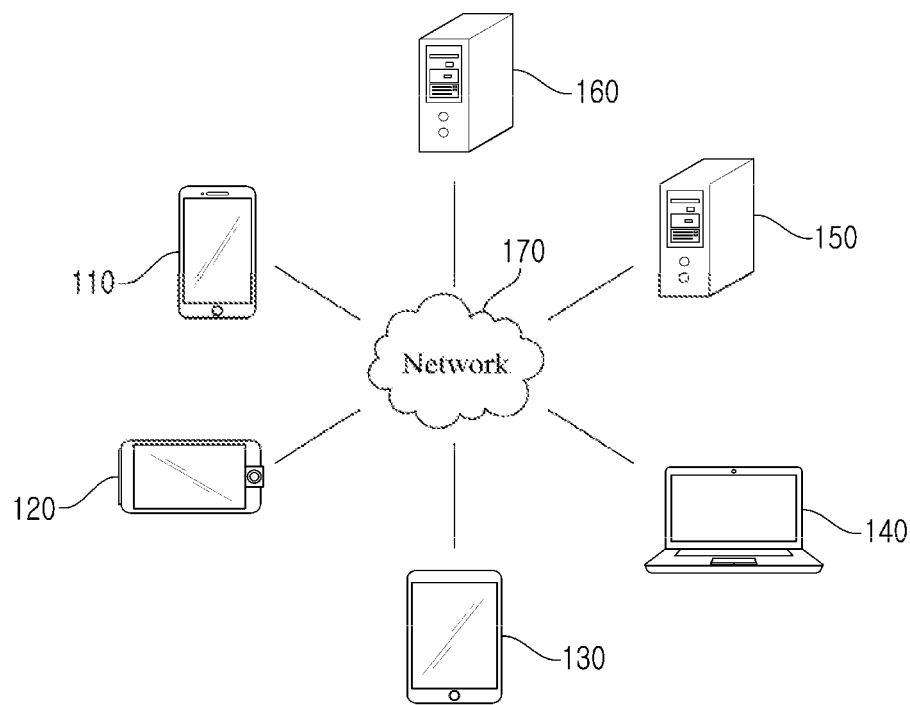
FIG. 1 is a diagram illustrating an example of a network environment according to at least one example embodiment.

It should be noted that these figures are intended to illustrate the general characteristics of methods and/or structure utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments.

DETAILED DESCRIPTION

One or more example embodiments will be described in detail with reference to the accompanying drawings. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated.

Although the terms "first," "second," "third," etc., may be used herein to describe various elements, components, regions, layers, and/or sections, these elements, components, regions, layers, and/or sections, should not be limited by these terms. These terms are only used to distinguish one element, component, region, layer, or section, from another region, layer, or section. Thus, a first element, component, region, layer, or section, discussed below may be termed a second element, component, region, layer, or section, without departing from the scope of this disclosure.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

As used herein, the singular forms "a," "an," and "the," are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups, thereof. As used herein, the term "and/or" includes any and all combinations of one or more of the associated listed products. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware and/or a combination of hardware and software. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor), Central Processing Unit (CPU), a controller, an arithmetic logic unit (ALU), a digital signal processor, a microcomputer, a microprocessor, etc., the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable storage mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive, solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blue-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Hereinafter, example embodiments will be described with reference to the accompanying drawings.

A user confidence building method according to the example embodiments may be performed by a computer apparatus, which is described below. For example, a computer program according to the example embodiments may be installed and run on the computer apparatus, and the computer apparatus may perform the user confidence building method according to the example embodiments. The computer program may be stored in a non-transitory computer-readable storage medium to implement the user confidence building method on a computer apparatus in conjunction with the computer apparatus. Here, the computer program may be in a form of a single independent program package or may be in a form in which a single independent program package is already installed in the computer apparatus and interworks with an operating system or other program packages.

FIG. 1 illustrates an example of a network environment according to at least one example embodiment. Referring to FIG. 1, the network environment may include a plurality of electronic devices 110, 120, 130, and 140, a plurality of servers 150 and 160, and a network 170. FIG. 1 is provided as an example only. A number of electronic devices or a number of servers is not limited thereto. Also, the network environment of FIG. 1 is provided to describe one example among environments applicable to the example embodiments. An environment applicable to the example embodiments is not limited to the network environment of FIG. 1.

Each of the plurality of electronic devices 110, 120, 130, and 140 may be a fixed terminal or a mobile terminal that is configured as a computer apparatus. For example, the plurality of electronic devices 110, 120, 130, and 140 may be a smartphone, a mobile phone, a navigation device, a computer, a laptop computer, a digital broadcasting terminal, a personal digital assistant (PDA), a portable multimedia player (PMP), a tablet PC, and the like. For example, although FIG. 1 illustrates a shape of a smartphone as an example of the electronic device 110, the electronic device 110 used herein may refer to one of various types of physical computer apparatuses capable of communicating with other electronic devices 120, 130, and 140, and/or the servers 150 and 160 over the network 170 in a wireless or wired communication manner.

The communication scheme is not limited and may include a near field wireless communication scheme between devices as well as a communication scheme using a communication network (e.g., a mobile communication network, wired Internet, wireless Internet, a broadcasting network) includable in the network 170. For example, the network 170 may include at least one of network topologies that includes a personal area network (PAN), a local area network (LAN), a campus area network (CAN), a metropolitan area network (MAN), a wide area network (WAN), a broadband network (BBN), and Internet. Also, the network may include at least one of network topologies that include a bus network, a star network, a ring network, a mesh network, a star-bus network, a tree or hierarchical network, and the like. However, they are provided as examples only.

Each of the servers 150 and 160 may be configured as a computer apparatus or a plurality of computer apparatuses that provides an instruction, a code, a file, content, a service, etc., through communication with the plurality of electronic devices 110, 120, 130, and 140 over the network 170. For example, the server 150 may be a system that provides a service (e.g., a messenger service, a social network service, a search service, a mail service, a content providing service, a voice recognition service, a financial service, a payment service, and a navigation service) to the plurality of electronic devices 110, 120, 130, and 140 connected over the network 170.

Figure 2:
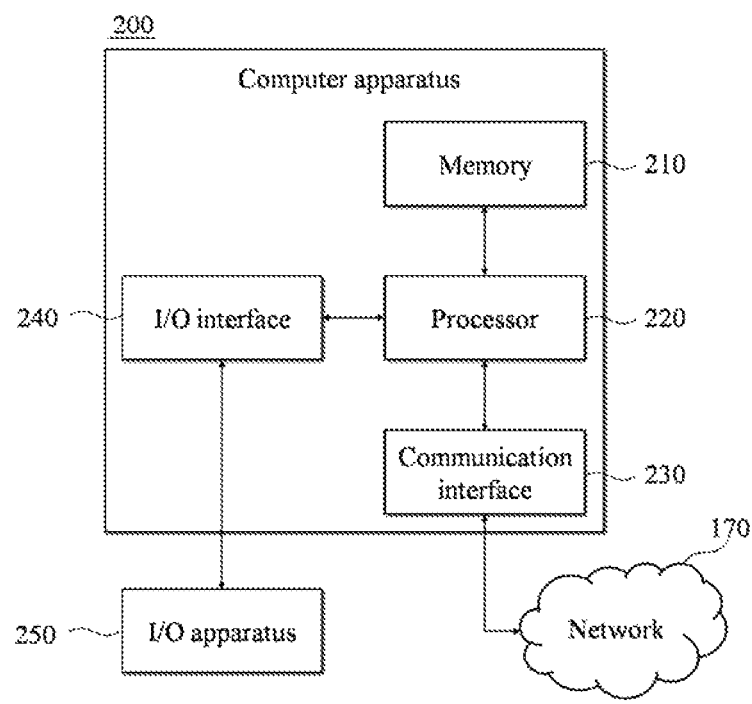
FIG. 2 is a diagram illustrating an example of a computer apparatus according to at least one example embodiment.

FIG. 2 is a block diagram illustrating an example of a computer apparatus according to at least one example embodiment. For example, each of the plurality of electronic devices 110, 120, 130, and 140 or each of the plurality of servers 150 and 160 may be implemented using a computer apparatus 200 of FIG. 2. A user confidence building method according to example embodiment may be performed by the computer apparatus 200.

Referring to FIG. 2, the computer apparatus 200 may include a memory 210, a processor 220, a communication interface 230, and an input/output (I/O) interface 240. The memory 210 may include a permanent mass storage device, such as random access (RAM), read only memory (ROM), and a disc drive, as a non-transitory computer-readable storage medium. Here, the permanent mass storage device, such as ROM and disc drive, may be included in the computer apparatus 200 as a separate permanent storage device different from the memory 210. Also, an operating system (OS) and at least one program code may be stored in the memory 210. Such software components may be loaded from another non-transitory computer-readable storage medium to the memory 210. The other non-transitory computer-readable storage medium may include a non-transitory computer-readable storage medium, for example, a floppy drive, a disk, a tape, a DVD/CD-ROM drive, a memory card, etc. According to other example embodiments, software components may be loaded to the memory 210 through the communication interface 230, instead of, or in addition to, the non-transitory computer-readable storage medium. For example, the software components may be loaded to the memory 210 of the computer apparatus 200 based on a computer program installed by files received over the network 170.

The processor 220 may be configured to process computer-readable instructions of a computer program by performing basic arithmetic operations, logic operations, and I/O operations. The computer-readable instructions may be provided from the memory 210 or the communication interface 230 to the processor 220. For example, the processor 220 may be configured to execute received instructions in response to a program code stored in a storage device, such as the memory 220.

The communication interface 230 may provide a function for communication between the computer apparatus 200 and another apparatus, for example, the aforementioned storage devices over the network 170. For example, the processor 220 of the computer apparatus 200 may transfer a request or an instruction created based on the program code stored in the storage device, such as the memory 220, to other apparatuses over the network 170 under control of the communication interface 230. Inversely, a signal, an instruction, data, a file, etc., from another apparatus may be received at the computer apparatus 200 through the communication interface 230 of the computer apparatus 200. For example, a signal, an instruction, data, etc., received through the communication interface 230 may be transferred to the processor 220 or the memory 210, and a file, etc., may be stored in a storage medium, for example, the permanent storage device, further includable in the computer apparatus 200.

The I/O interface 240 may be a device used for interface with an I/O apparatus 250. For example, an input device may include a device, such as a microphone, a keyboard, and a mouse, and an output device may include a device, such as a display device and a speaker. As another example, the I/O interface 240 may be a device for interface with an apparatus in which an input function and an output function are integrated into a single function, such as a touchscreen. The I/O apparatus 250 may be configured as a single apparatus with the computer apparatus 200.

According to other example embodiments, the computer apparatus 200 may include a number of components greater than or less than a number of components shown in FIG. 2. However, there is no need to clearly illustrate many components according to the related art. For example, the computer apparatus 200 may include at least a portion of the I/O apparatus 250, or may further include other components, for example, a transceiver, a database (DB), and the like.

Figure 3:
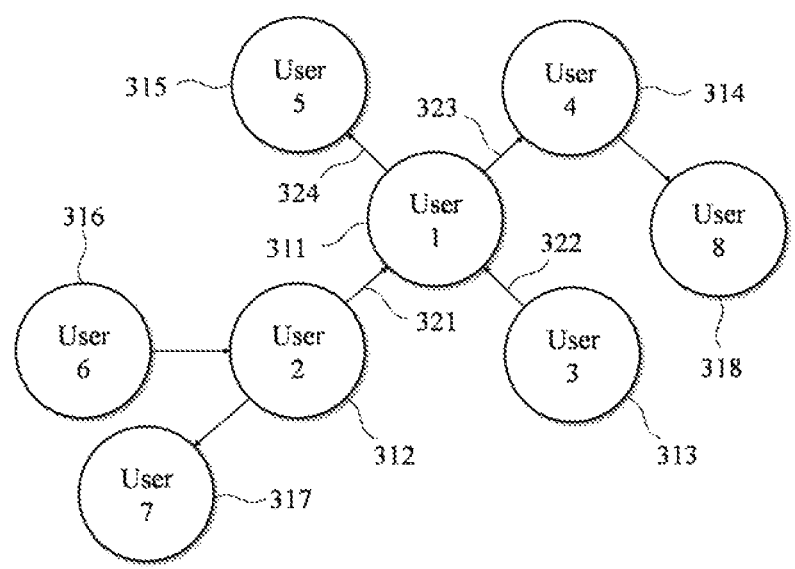
FIG. 3 illustrates an example of an incoming edge and an outgoing edge according to an example embodiment.

FIG. 3 illustrates an example of an incoming edge and an outgoing edge according to an example embodiment. At a service, for example, a social network service (SNS), an activity of each of users generally has a source and a target and also has a directivity. For example, an activity that a first user views a posting of a second user has a directivity from the first user toward the second user. Here, the first user may be a source and a second user may be a target. That is, the activity that the first user views the posting of the second user differs from an activity that the second user views a posting of the first user in terms of a source, a target, and an activity. The activities may be classified as different activities of the same attribute. Referring to FIG. 3, a source, a target, and a directivity between a plurality of users, for example, a user 1 311 to a user 8 318, are represented using an indicator (hereinafter, referred to as an arrow) with an arrowhead.

For example, an arrow 321 represents a directivity of an activity of the user 2 312 toward the user 1 311 and also represents that the user 2 312 is a source and the user 1 311 is a target. The activity of the user 2 312 may be an activity index in terms of passiveness of the user 1 311. Here, from perspective of the user 1 311, the activity index in terms of passiveness may be defined as an incoming edge. In FIG. 3, arrows 321 and 322 toward the user 1 311 may represent incoming edges of the user 1 311. Inversely, an arrow 323 from the user 1 311 toward the user 4 314 represents a directivity of an activity of the user 1 311 toward the user 4 314 and also represents that the user 1 311 is a source and the user 4 314 is a target. The activity of the user 1 311 may be an activity index in terms of activeness of the user 1 311.

From perspective of the user 1 311, the activity index in terms of activeness may be defined as an outgoing edge. Here, in FIG. 3, arrows 323 and 324 starting from the user 1 311 may represent outgoing edges of the user 1 311. That is, the arrow 321 may represent an incoming edge from perspective of the user 1 311 and may represent an outgoing edge from perspective of the user 2 312.

Meanwhile, a single edge may correspond to a single activity. For example, in FIG. 3, a single arrow may correspond to a single edge and accordingly, the single arrow may correspond to a single activity. If a new activity of the user 2 312 toward the user 1 311 is generated, an arrow from the user 2 312 toward the user 1 311 may be added to represent this event in the aforementioned representation manner.

According to example embodiments, a confidence of a specific user may be adjusted based on an incoming edge of the corresponding user. As described above, since an outgoing edge is adjustable based on the intent of the user, a confidence according to the outgoing edge may have a degraded objectivity and may have a relatively high abusing probability. In contrast, since the incoming edge represents an activity of another user toward the corresponding user and has a relatively low probability of being adjusted based on the intent of the user, a confidence according to the incoming edge may secure an objectivity and may have a relatively low abusing probability.

Meanwhile, in FIG. 3, the plurality of users 1 311 to 8 318 may correspond to user accounts for identifying actual users at a service, instead of corresponding to the actual users. That is, an arrow is used to describe a source, a target, and a directivity according to an activity between user accounts. Forwarding and propagation of a confidence, which is described below, may correspond to not physical movement or transmission of data between devices through a network but identification of a parameter for confidence calculation. For example, forwarding an adjusted confidence of the user 2 312 to the user 1 311 may correspond to, that is, represent that the adjusted confidence of the user 2 312 is forwarded to a function for readjusting a confidence of the user 1 311 as a parameter to readjust the confidence of the user 1 311.

Figure 4:
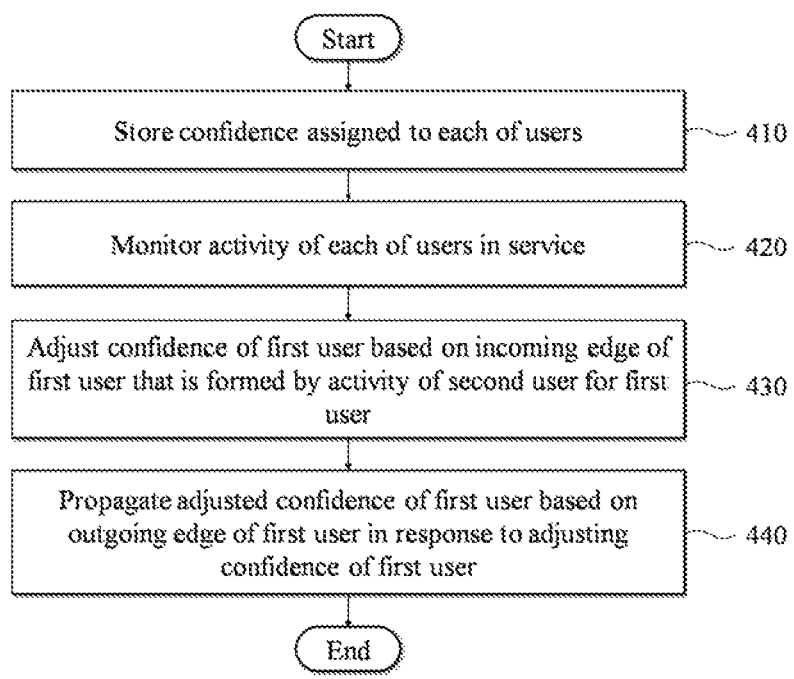
FIG. 4 is a flowchart illustrating an example of a user confidence building method according to at least one example embodiment.

FIG. 4 is a flowchart illustrating a user confidence building method according to at least one example embodiment. The user confidence building method of FIG. 4 may be performed by the aforementioned computer apparatus 200. For example, the processor 220 of the computer apparatus 200 may be configured to execute a control instruction according to a code of at least one program or a code of an OS included in the memory 210. Here, the processor 220 may control the computer apparatus 200 to perform operations 410 to 440 included in the method of FIG. 4 in response to the control instruction provided from a code stored in the computer apparatus 200.

Referring to FIG. 4, in operation 410, the computer apparatus 200 may store a confidence assigned to each of users. Initial confidences of the users may be assigned as predefined default values and may be adjusted based on incoming edges of the respective users.

In operation 420, the computer apparatus 200 may monitor an activity of each of the users in a social network. In particular, the computer apparatus 200 may monitor the activity to acquire information about a source, a target, and a directivity of the activity to determine a user of which an incoming edge the activity corresponds to.

In operation 430, the computer apparatus 200 may adjust a confidence of a first user based on an incoming edge of the first user that is formed by an activity of a second user for the first user.

For example, the computer apparatus 200 may determine an adjustment level of the confidence of the first user based on at least one of an attribute of the activity of the second user that forms the incoming edge and a confidence of the second user. Here, the attribute of the activity may include at least one of a type of the activity and content of the activity. For example, the content of the activity may include a text such as a comment, an emoticon, and an image, which are created online, that is, registered by a user in response to an action of the user. Here, an activity that includes content may be used to determine an attribute of the activity corresponding to the content by additionally determining information, such as positiveness (positive attribute) of the content or negativity (negative attribute of the content. For example, as described above with FIG. 3, an activity that the first user views a posting of the second user may differ from an activity that the second user views a posting of the first user in terms of a source, a target, and a directivity and the activities may be classified as different activities. Here, if confidences of users corresponding to a source are identical, activities of the same attribute may be determined to have the same adjustment level for the confidence and an adjustment level for a confidence may vary based on an attribute of a corresponding activity. Meanwhile, according to an increase in a confidence of the second user, an adjustment level for the confidence of the first user may relatively increase. For example, with respect to activities of second users corresponding to the same attribute, an adjustment level for the confidence of the first user may vary based on confidences of the second users. Also, the computer apparatus 200 may increase the confidence of the first user based on a positive activity of the second user for the first user and may decrease the confidence of the first user based on a negative activity of the second user for the first user. That is, a confidence of a corresponding user may increase according to an increase in a number of incoming edges according to a positive activity, and the confidence of the user may decrease according to an increase in a number of incoming edges according to a negative activity. For example, the positive activity may include at least one activity among a (1-1)-th activity that the second user initially sends a message to the first user, a (1-2)-th activity that the second user adds the first user as a personal relationship of a social network, a (1-3)-th activity that the second user invites the first user to a chatroom or a community in which the second user participates, a (1-4)-th activity that the second user adds the first user to favorite, and a (1-5)-th activity that the second user creates a comment on a posting of the first user. Also, the negative activity may include at least one activity among a (2-1)-th activity that a frequency at which the second user sends a message to the first user decreases, a (2-2)-th activity that the second user excludes the first user from the personal relationship of the social network, a (2-3)-th activity that the second user excludes the first user from the chatroom or the community in which the second user participates, a (2-4)-th activity that the second user excludes the first user from the favorite, and a (2-5)-th activity that the second user deletes the comments created by the second user on the posting of the first user. Here, each of the (1-1)-th activity to the (1-5)-th activity and the (2-1) activity to the (2-5)-th activity may be a portion of types of each corresponding activity.

If the second user registers the first user as a friend of a service, for example, a social network service, a confidence of the first user may increase by an adjustment level that is determined based on an attribute of the (1-2) activity and a confidence of the second user. Then, if the second user excludes the first user from the friend of the service, the confidence of the first user may decrease by an adjustment level that is determined based on an attribute of the (2-2) activity and the confidence of the second user.

As described above, since the confidence of the first user is adjusted based on not the activity of the first user but an incoming edge that is an activity index in terms of passiveness of the first user, the objectiveness for the confidence of the first user may be secured.

In operation 440, the computer apparatus 200 may propagate the adjusted confidence of the first user based on an outgoing edge of the first user in response to adjusting the confidence of the first user. For example, the outgoing edge of the first user may be an incoming edge of a third user that is a target of the activity of the first user. That is, a confidence of the third user may be adjusted based on the activity of the first user. Here, an adjustment level may be affected by the confidence of the first user. Accordingly, if the confidence of the first user is adjusted, the adjusted confidence of the first user may be propagated through the outgoing edge of the first user to apply the adjusted confidence of the first user to other user. In this case, the third user may readjust the confidence of the third user based on the adjusted confidence of the first user. Likewise, adjusting the confidence of the third user may be connected to readjusting a confidence of a fourth user that is a target of an activity of the third user. That is, adjusting a confidence of a user may be sequentially propagated to consecutively linked other users through an outgoing edge.

Likewise, the confidence of the first user may be readjusted. For example, if the confidence of the second user is adjusted, the adjusted confidence of the second user may be propagated to the first user through an outgoing edge of the second user. In this case, in response to adjusting the confidence of the second user, the computer apparatus 200 may readjust the confidence of the first user based on the adjusted confidence of the second user that is propagated through an incoming edge of the first user. That is, a confidence change of an evaluator may connect to readjusting a confidence of a user to be evaluated.

Meanwhile, confidences of users may be further adjusted based on a penalty at a service. For example, in operation 430, the computer apparatus 200 may readjust the confidence of the first user in response to imposing a penalty to the first user at the service. As another example, in operation 430, the computer apparatus 200 may readjust the confidence of the first user based on an adjusted confidence of the second user that is propagated through the incoming edge of the first user as the confidence of the second user is readjusted in response to imposing a penalty to the second user at the service. Here, although a different penalty may be imposed for each service, the penalty may be imposed to users in various situations, such as sending a message using a bot, registering a friend, or a user being a spammer. A confidence readjusted through the penalty at the service may be propagated through an outgoing edge of a corresponding user.

Also, the computer apparatus 200 may adjust a rate at which the adjusted confidence is propagated based on an attribute of an activity. The rate of propagation may affect a point in time at which a confidence of each user is adjusted. The confidence of each user may be used to determine a confidence of other user. Also, the confidence may comprise each user's credit rating.

Further, a change in the point in time at which the confidence is readjusted may affect the user evaluation in conjunction with a point in time at which the confidence of the user is determined. For example, the computer apparatus 200 may adjust a rate at which the adjusted confidence of the first user is propagated based on an attribute of the activity of the second user for the first user. Here, if an activity has an attribute of which influence is relatively great, the adjusted confidence may be propagated relatively faster. For example, the (2-2)-th activity that the second user excludes the first user from the personal relationship at the service may be set to have an influence greater than that of the (2-1)-th activity that a frequency at which the second user sends a message to the first user decreases. In this case, a propagation rate of a confidence adjusted based on the (2-2)-th activity may be relatively faster compared to that of the confidence adjusted based on the (2-1)-th activity. That is, if a user is periodically evaluated based on a confidence of the user, an adjusted confidence of a relatively fast propagation rate is relatively highly likely to apply to a user evaluation in a current period and an adjusted confidence of a relatively slow propagation rate is relatively less likely to apply to a user evaluation in a current period. Also, the adjusted confidence of the low propagation rate may be likely to be offset by other confidence adjustment.

Also, in one example embodiment, the computer apparatus 200 may determine whether the first user is an abuser based on the adjusted confidence of the first user. For example, if the first user has a relatively large number of outgoing edges and barely has an incoming edge, a confidence of the first user may be relatively very low and the first user is likely to be an abuser. Inversely, the computer apparatus 200 may determine the first user as a reliable user based on the adjusted confidence of the first user. Also, the computer apparatus 200 may determine a new service to be provided to the first user based on the adjusted confidence of the first user. For example, an available service may be predetermined based on a grade that is determined through the confidence scope. Also, the computer apparatus 200 may open the confidence to users such that the users may use the confidence for adding a friend or inviting another user to a community. For example, a confidence of a user that is determined based on an activity of another user may represent a popularity of the user. Also, the computer apparatus 200 may determine a ranking based on the confidence and may provide a user list according to the determined rankings to the users. The computer apparatus 200 may provide rewards to the users based on the confidences. For example, a preset reward may be provided to each corresponding user based on the aforementioned ranking. The confidence of the user that is determined according to the example embodiments may be variously used.

According to example embodiments, the computer apparatus 200 may adjust and determine a confidence and the determined confidence may be used through another entity.

Figure 5:
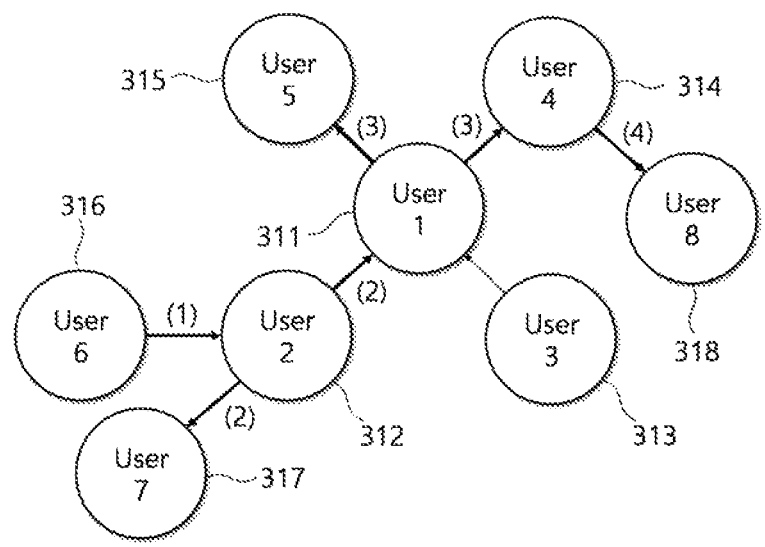
FIG. 5 illustrates an example of a propagation path of an adjusted confidence according to at least one example embodiment.

FIG. 5 illustrates an example of a propagation path of an adjusted confidence according to at least one example embodiment. Similar to the example embodiment of FIG. 3, FIG. 5 illustrates the plurality of users, for example, user 1 311 to user 8 318. Here, it is assumed that a confidence of the user 6 316 is adjusted. In this case, referring to (1) of FIG. 5, the adjusted confidence of the user 6 316 may be forwarded to the user 2 312. The adjusted confidence of the user 6 316 forwarded to the user 2 312 causes a confidence of the user 2 312 to be readjusted. Referring to (2), in response to readjusting the confidence of the user 2 312, the readjusted confidence may be forwarded to the user 1 311 and the user 7 317. The adjusted confidence of the user 2 312 that is forwarded to the user 1 311 and the user 7 317 causes a confidence of each of the user 1 311 and the user 7 317 to be readjusted. In FIG. 5, since the user 7 317 does not have an outgoing edge, the adjusted confidence of the user 7 317 is not forwarded. In contrast, referring to (3), the adjusted confidence of the user 1 311 may be forwarded to the user 4 314 and the user 5 315 through outgoing edges of the user 1 311 (3). The adjusted confidence of the user 1 311 forwarded to the user 4 314 and the user 5 315 causes a confidence of each of the user 4 314 and the user 5 315 to be readjusted. In FIG. 5, since the user 5 315 does not have an outgoing edge, the adjusted confidence of the user 5 315 is not forwarded. In contrast, referring to (4), the adjusted confidence of the user 4 314 may be forwarded to the user 8 318 through an outgoing edge of the user 4 314 and may cause the confidence of the user 8 318 to be adjusted. As described above, the adjusted confidence may be sequentially propagated through an outgoing edge.

As described above, according to example embodiments, the objectivity about a confidence may be secured by adjusting a confidence of a user based on an incoming edge of the user that is formed by an activity of another user for the user and by evaluating the user based on actions in terms of passiveness of the user, which are activities of other users for the user.

The systems or the apparatuses described herein may be implemented using hardware components, software components, and/or a combination thereof. For example, a processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, for independently or collectively instructing or configuring the processing device to operate as desired. Software and data may be embodied permanently or temporarily in any type of machine, component, physical equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable storage mediums.

The methods according to the example embodiments may be recorded in non-transitory computer-readable storage media including program instructions to implement various operations embodied by a computer. The media may also include, alone or in combination with the program instructions, data files, data structures, and the like. The media and program instructions may be those specially designed and constructed for the purposes, or they may be of the kind well-known and available to those having skill in the computer software arts. Examples of non-transitory computer-readable storage media include magnetic media such as hard disks, floppy disks, and magnetic tape; optical media such as CD ROM disks and DVD; magneto-optical media such as floptical disks; and hardware devices that are specially to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be to act as one or more software modules in order to perform the operations of the above-described embodiments, or vice versa.

The foregoing description has been provided for purposes of illustration and description. It is not intended to be exhaustive or to limit the disclosure. Individual elements or features of a particular example embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method comprising:
   by at least one processor,
   storing, for each user of a plurality of users of a service provided through electronic devices, information indicating a confidence assigned to the user that represents an evaluation of the user based on monitored activities of the user in the service;
   forming an incoming edge for a first user, among the plurality of users, based on monitoring an activity of a second user, among the plurality of users, that represents a directed activity in the service of the second user towards the first user;
   adjusting a confidence of the first user indicated by the stored information based on the formed incoming edge;
   based on the adjusted confidence of the first user, forming an outgoing edge for the first user that represents a directed activity in the service towards another user, among the plurality of users; and
   propagating the adjusted confidence of the first user in the stored information based on the formed outgoing edge for the first user.

2. The method of claim 1, wherein the forming of the incoming edge for the first user comprises determining an adjustment level of the confidence of the first user based on at least one of an attribute of the monitored activity of the second user, and a confidence of the second user indicated by the stored information that is based on the monitored activity of the second user.

3. The method of claim 1, wherein the forming of the incoming edge for the first user comprises determining an adjustment level to increase the confidence of the first user based on the monitored activity of the second user being indicated as a positive activity of the second user towards the first user, and determining an adjustment level to decrease the confidence of the first user based on the monitored activity of the second user being indicated as a negative activity of the second user towards the first user.

4. The method of claim 3, wherein the positive activity comprises at least one positive activity among a first positive activity that the second user initially sends a message to the first user, a second positive activity that the second user adds the first user as a personal relationship at the service, a third positive activity that the second user invites the first user to a chatroom or a community in which the second user participates, a fourth positive activity that the second user adds the first user as a favorite, and a fifth positive activity that the second user creates a comment on a posting of the first user, and
   the negative activity comprises at least one negative activity among a first negative activity that a frequency at which the second user sends a message to the first user decreases, a second negative activity that the second user excludes the first user from a personal relationship at the service, a third negative activity that the second user excludes the first user from a chatroom or a community in which the second user participates, a fourth negative activity that the second user excludes the first user from a favorite, and a fifth negative activity that the second user deletes the comment created by the second user on the posting of the first user.

5. The method of claim 1, wherein the propagating of the adjusted confidence of the first user comprises readjusting a confidence of the another user indicated by the stored information, based on the formed outgoing edge for the first user.

6. The method of claim 1, further comprising:
   readjusting the confidence of the first user based on an adjusted confidence of the second user that is propagated in the stored information through a formed outgoing edge of the second user that represents a directed activity in the service towards the first user.

7. The method of claim 1, further comprising readjusting the confidence of the first user in response to imposing a penalty to the confidence of the first user at the service, or readjusting the confidence of the first user based on an adjusted confidence of the second user that is propagated through an outgoing edge of the second user formed based on the readjusted confidence of the second user in response to imposing a penalty to the confidence of the second user at the service.

8. The method of claim 1, wherein the propagating of the adjusted confidence of the first user comprises adjusting a rate at which the adjusted confidence of the first user is propagated based on an attribute of the monitored activity of the second user.

9. The method of claim 1, further comprising:
   determining whether the first user is to be indicated as an abuser based on the adjusted confidence of the first user.

10. The method of claim 1, further comprising:
    determining another service to be provided to the first user based on the adjusted confidence of the first user.

11. A non-transitory computer-readable storage medium storing computer instructions that, when executed by a processor, cause the processor to perform the method of claim 1.

12. A computer apparatus comprising:
    at least one processor configured to execute a computer-readable instruction,
    wherein the at least one processor is configured to,
    store for each user of a plurality of users of a service provided through electronic devices, information indicating a confidence assigned to the user that represents an evaluation of the user based on monitored activities of the user in the service, form an incoming edge for a first user, among the plurality of users, based on monitoring an activity of a second user, among the plurality of users, that represents a directed activity in the service of the second user towards the first user;

adjust a confidence of the first user indicated by the stored information based on the formed incoming edge, based on the adjusted confidence of the first user, form an outgoing edge for the first user that represents a directed activity in the service towards another user, among the plurality of users; and propagate the adjusted confidence of the first user in the stored information based on the formed outgoing edge for the first user.

13. The computer apparatus of claim 12, wherein to form the incoming edge for the first user, the at least one processor is configured to determine an adjustment level of the confidence of the first user based on at least one of an attribute of the monitored activity of the second user, and a confidence of the second user indicated by the stored information that is based on the monitored activity of the second user.

14. The computer apparatus of claim 12, wherein to form the incoming edge for the first user, the at least one processor is configured to determine an adjustment level to increase the confidence of the first user based on the monitored activity of the second user being indicated as a positive activity of the second user towards the first user, and determine an adjustment level to decrease the confidence of the first user based on the monitored activity of the second user being indicated as a negative activity of the second user towards the first user.

15. The computer apparatus of claim 12, wherein to propagate the adjusted confidence of the first user, the at least one processor is configured to readjust a confidence of the another user indicated by the stored information, based on the formed outgoing edge for the first user.

16. The computer apparatus of claim 12, wherein the at least one processor is configured to readjust the confidence of the first user based on an adjusted confidence of the second user that is propagated in the stored information through a formed outgoing edge of the second user that represents a directed activity in the service towards the first user.

17. The computer apparatus of claim 12, wherein the at least one processor is configured to readjust the confidence of the first user in response to imposing a penalty to the confidence of the first user at the service, or readjusting the confidence of the first user based on an adjusted confidence of the second user that is propagated through an outgoing edge of the second user formed based on the readjusted confidence of the second user in response to imposing a penalty to the confidence of second user at the service.

18. The computer apparatus of claim 12, wherein to propagate the adjusted confidence of the first user, the at least one processor is configured to readjust a rate at which the adjusted confidence of the first user is propagated based on an attribute of the monitored activity of the second user.

* * * * *